United States Patent [19]

Dean et al.

[11] Patent Number: 5,700,835
[45] Date of Patent: Dec. 23, 1997

[54] 3-OXA-D-PROSTAGLANDINS FOR LOWERING IOP

[75] Inventors: Thomas R. Dean, Weatherford; Mark Hellberg, Arlington; Verney L. Sallee, Southlake, all of Tex.

[73] Assignee: Alcon Laboratories, Inc., Fort Worth, Tex.

[21] Appl. No.: 577,037

[22] Filed: Dec. 22, 1995

[51] Int. Cl.$^6$ .......................... A61K 31/215; A61K 31/19
[52] U.S. Cl. .......................... 514/530; 514/573; 514/913
[58] Field of Search .................. 514/530, 573, 514/913

[56] References Cited

U.S. PATENT DOCUMENTS

| | | |
|---|---|---|
| 4,097,489 | 6/1978 | Bundy . |
| 4,599,353 | 7/1986 | Bito . |
| 5,296,504 | 3/1994 | Stjernschantz et al. . |

FOREIGN PATENT DOCUMENTS

| | | |
|---|---|---|
| 0 115 844 A | 8/1984 | European Pat. Off. . |
| 0 299 914 A1 | 1/1989 | European Pat. Off. . |
| 0 569 046 A1 | 11/1993 | European Pat. Off. . |
| 0 364 417 B1 | 2/1994 | European Pat. Off. . |
| WO 90/02553 | 3/1990 | WIPO . |
| WO 94/05631 | 3/1994 | WIPO . |
| WO 94/06433 | 3/1994 | WIPO . |

OTHER PUBLICATIONS

Goh, Effects Of Prostaglandin $D_2$ and Its Analogues On Intraocular Pressure In Rabbits, *Jpn J. Ophthalmol.*, vol. 32, pp. 471–480 (1988).

Goh, Effect of topical prostaglandin $D_2$ on the aqueous humor dynamics in rabbits, *Graefe's Archive Clin. Exp. Ophthalmology*, vol. 227, pp. 476–481 (1989).

Thierauch, Prostaglandins and their Receptors: II. Receptor and Signal Transduction, *Journal of Hypertension*, vol. 12, pp. 1–5 (1994).

Nakajima, Effects of Prostaglandin $D_2$ and its analogue, BW245C, on Intraocular Pressure in Humans, *Graefe's Archive Ophthalmology*, vol. 229, pp. 411–413 (1991).

Bundy, Synthesis and Platelet Aggregation Inhibiting Activity of Prostaglandin D Analogues, *Journal of Medicinal Chemistry*, vol. 26, pp. 790–799 (1983).

Alm, The Potential of Prostaglandin Derivatives in Glaucoma Therapy, *Current Opinion in Ophthalmology*, vol. 4, No. 11, pp. 44–50 (1993).

Sharif, Affinities of Muscarinic Drugs for [$^3$H]N–Methylscopolamine (NMS) and [$^3$H]Oxotremorine (OXO) Binding to a Mixture of $M_1$–$M_4$ Muscarinic Receptors: Use of NMS/OXO–M Ratios to Group Compounds into Potential Agonist, Partial Agonist, and Antagonist Classes, *Neurochemistry Research*, vol. 20, No. 6, pp. 669–674 (1995).

Sharif, Emedastine: A Potent, High Affinity Histamine $H_1$—Receptor–Selective Antagonist for Ocular Use: Receptor Binding andSecond Messenger Studies, *Journal of Ocular Pharmacology*, vol. 10, No. 4, pp. 653–664 (1994).

Barraclough, Synthesis and Platelet Aggregation Inhibiting Activity of Acid Side–chain Modified Hydantoin Prostaglandin Analogues, *Archives in Pharmacology*, vol. 326, No. 2, pp. 85–95 (1993).

Jagabandhu Das et al., 9,11–Epoxy–9–homoprosta–5–enoic acid analogues as thromboxane A2 receptor antagonists,, .*Med. Chem.*, vol. 33, pp. 1741–1748 (1990).

Thierauch et al., Prostaglandin D2 and its analogs, *Drugs of The Future*, vol. 17, No. 9, p. 811, left–hand col., paragraph 4, figure 3 (1994).

*Primary Examiner*—Zohreh Fay
*Attorney, Agent, or Firm*—Michael C. Mayo

[57] ABSTRACT

Compositions containing 3-Oxa-D-prostaglandins and methods of their use in treating glaucoma or ocular hypertension are disclosed.

8 Claims, No Drawings

3-OXA-D-PROSTAGLANDINS FOR LOWERING IOP

The present invention relates to the treatment of glaucoma and ocular hypertension. In particular, the present invention relates to the use of certain prostaglandin D-series compounds to treat glaucoma and hypertension.

BACKGROUND OF THE INVENTION

Glaucoma is a progressive disease which leads to optic nerve damage, and, ultimately, total loss of vision. The causes of this disease have been the subject of extensive studies for many years, but are still not fully understood. The principal symptom of and/or risk factor for the disease is elevated intraocular pressure or ocular hypertension due to excess aqueous humor in the anterior chamber of the eye.

The reasons why aqueous humor accumulates are not fully understood. It is known that the elevated intraocular pressure ("IOP") can be at least partially controlled by administering drugs which reduce either the production of aqueous humor within the eye, such as beta-blockers and carbonic anhydrase inhibitors, or increase the flow of aqueous humor out of the eye, such as miotics and sympathomimetics.

All types of drugs currently being used to treat glaucoma have potentially serious side effects. Miotics such as pilocarpine can cause blurring of vision and other visual side effects, which may lead either to decreased patient compliance or to termination of therapy. Systemically administered carbonic anhydrase inhibitors can also cause serious side effects, such as nausea, dyspepsia, fatigue, and metabolic acidosis which can affect patient compliance and/or necessitate the withdrawal of treatment. Moreover, some beta-blockers have increasingly become associated with serious pulmonary side effects attributable to their effects on beta-2 receptors in pulmonary tissue. Sympathomimetics cause tachycardia, arrhythmia and hypertension. There is therefore a continuing need for therapies which control the elevated intraocular pressure associated with glaucoma.

Prostaglandins, which are metabolite derivatives of arachidonic acid, have recently been pursued for possible efficacy in lowering IOP. The arachidonic acid cascade is initiated by the conversion of arachidonic acid to prostaglandin $G_2$ and subsequent conversion to prostaglandin $H_2$. Other naturally occurring prostaglandins are derivatives of prostaglandin $H_2$. A number of different types of prostaglandins have been discovered including A, B, D, E, F and I-Series prostaglandins. Of interest in the present invention are compounds which exhibit similar IOP lowering mechanisms as $PGD_2$ (a D-series prostaglandin) shown in formula (I):

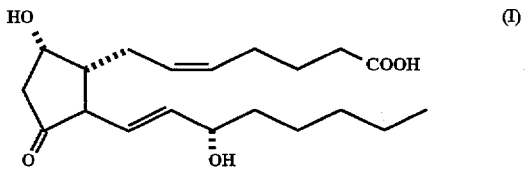

The relationship of $PGD_2$ receptor activation and IOP lowering effects is not well known, but the IOP lowering effect is thought to be due to activation of the $PGD_2$ receptor. Various publications have reported that $PGD_2$ receptor activation leads to second messenger activation and in particular, to the stimulation of adenylate cyclase and resultant increases in cAMP levels (Thierauch, *Prostaglandins and their Receptors: II. Receptor Structure and Signal Transduction, Journal of Hypertension*, volume 12, pages 1–5 (1994). Regardless of mechanism, $PGD_2$ has been shown to lower IOP (Nakajima, *Effects of Prostaglandin $D_2$ and its analogue, BW245C, on Intraocular Pressure in Humans, Graefe's Archive Ophthalmology*, volume 229, pages 411–413 (1991)). Thus, it has been of interest in the field to develop synthetic PGD2 analogs with IOP lowering efficacy.

Synthetic $PGD_2$-type analogs have been pursued in the art (*Graefe's Archive Ophthalmology*, volume 229, pages 411–413 (1991)). Though $PGD_2$, BW245C and these synthetic analogs lower IOP, they have also been associated with undesirable side effects which are thought to arise from activation of other prostaglandin receptors within the eye. Such effects include an initial increase in IOP, conjunctival hyperemia, increases in microvascular permeability, and increases in eosinophile infiltration (Alm, *The Potential of Prostaglandin Derivatives in Glaucoma Therapy, Current Opinion in Ophthalmology*, volume 4, No. 11, pages 44–50 (1993)). The activation of the $PGD_2$ receptor with other types of molecules may lead to IOP lowering effects, but with fewer or reduced side effects as those analogs discussed above. Therefore, a need exists for the development of agonists that will bind the $PGD_2$ receptor, which are more efficacious in lowering IOP and exhibiting fewer or reduced side effects.

Certain 3-oxa-D-prostaglandins have been disclosed in WIPO Publication No. WO 94/05631.

SUMMARY OF THE INVENTION

The present invention is directed to compositions and methods of their use in treating IOP and ocular hypertension. In particular, the present invention provides certain classes of 3-Oxa-D-prostaglandins having functional $PGD_2$ receptor agonist activity, and methods of their use in treating glaucoma and ocular hypertension.

DETAILED DESCRIPTION OF THE INVENTION

It has unexpectedly been found that 3-Oxa-D-prostaglandins ("3-O-DP") are more efficacious in lowering and controlling IOP than their 3-carba analogs. Consequently, these 3-O-DPs can be administered at lower doses than their 3-carba analogs. The lower doses are believed to reduce their activity on other prostaglandin receptors and thereby reduce many of the aforementioned undesirable side effects.

The 3-O-DPs of the present invention are functionally defined by their ability to bind to prostaglandin-$D_2$ receptors of cells and evoke similar responses as when $PGD_2$ binds to these receptors. As used herein, "DP-agonists" refer to any agent which will bind to $PGD_2$ receptors and evoke cellular action in a similar way as $PGD_2$, to the extent that the binding leads to the lowering of IOP. Various assays may be used for the determination of DP-agonists, including those described below.

Binding assays may be used to elucidate DP-agonists of the present invention. Sharif has described a receptor binding assay in: Sharif, N. A., Williams, G. W. and DeSantis, L. M., *Neurochemistry Research*, volume 20, pages 669–674 (1995), the entire contents of which are incorporated herein by reference, and may be modified as described below, for the elucidation of DP-agonists of the present invention. Briefly, the binding assays are conducted in 25 mM Tris HCl (pH 7.4) containing 138 mM NACl, 5 mM $MgCl_2$, and 1 mM EDTA. Frozen-thawed expired human blood platelets (40–60 mg/ml stock) are incubated in a total volume of 500 μl with 2–10 nM [$^3$H]PGD$_2$ in the absence and presence of 100 μM unlabeled PGD$_2$ to define total and non-specific binding, respectively. The incubations (20 minutes at 23° C.) are terminated by rapid vacuum filtration, using a Whatman GF/B glass fiber filter previously soaked in 1% polyethyleneimine and 0.1% B SA, and the receptor-bound radioactivity is then determined by scintillation spectrometry. The binding data are analyzed using a non-linear, iterative curve-fitting computer program to define the receptor binding affinity ($K_i$) of the compounds. Compounds which exhibit $K_i$ values in this assay of less than or equal to about 20 μM are within the definition of DP-agonists of the present invention.

The DP-agonists of the present invention may also be defined functionally, by their ability to stimulate adenylate cyclase activity. Sharif has described this type of functional assay in: Sharif, N. A., Xu, S. and Yanni, J. M., *Journal of Ocular Pharmacology*, volume 10, pages 653–664 (1994), the entire contents of which are incorporated herein by reference, and which may be modified as described below, for the elucidation of DP-agonists of the present invention. Briefly, functional adenylate cyclase activity is determined using embryonic bovine tracheal cells (EbTr) cells. Cultured cells are stimulated with the test compound for 15 minutes at 23° C. The reaction is then stopped and the cAMP generated is determined by a radioimmunoassay kit. Data are analyzed using a non-linear, iterative curve-fitting computer program to define the potency ("EC$_{50}$", concentration which produces 50% of the maximum response of PGD$_2$) and efficacy of the compounds. Compounds which exhibit EChd50 values of less than or equal to about 10 μM are within the DP-agonist definition of the present invention.

The 3-O-DPs of the present invention are within the preceding DP-agonist definition, and are of the following formula (II):

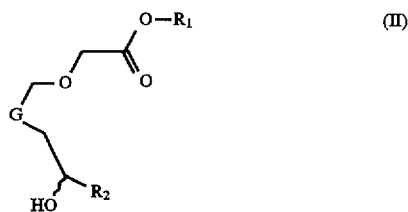

wherein:

R$_1$ is H, alkyl or alkylcycloalkyl;

R$_2$ is alkyl, cycloalkyl or alkylcycloalkyl; and

G is

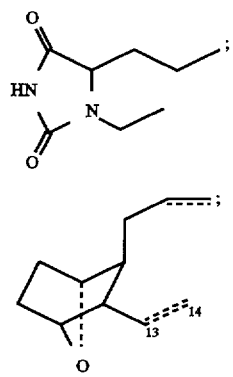

-continued

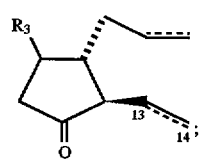

wherein:

R$_3$ is H, OH or alkyl;

----- represents a single bond or double bond; provided that double bonds between the 13 and 14 positions are in the trans configuration; and pharmaceutically acceptable salts thereof. Preferred DP-agonists of the present invention are those coming esters (i.e., R$_1$ is alkyl or alkylcycloalkyl), and wherein R$_2$ is cyclohexyl. Most preferred compounds of the present invention are those wherein R$_1$ is isopropyl. Some of the 3-O-DPs of the present invention are believed to be novel.

The 3-O-DPs, wherein G is formula (i), are described in Barraclough, *Synthesis and Platelet Aggregation Inhibiting Activity of Acid Side-chain Modified Hydantoin Prostaglandin Analogues, Archives in Pharmacology*, volume 326, No. 2, pages 85–95 (1993), the entire contents of which are incorporated herein by reference.

The 3-O-DPs, wherein G is formula (ii), may be prepared from [1S-[1α, 2α(Z), 3α(1E, 3S), 4α]]-7-[3-(3-Cyclohexyl-3-hydroxy-1-propenyl)-7-oxabicyclo[2.2.1]hept-2-yl]-5-heptenoic acid following the procedure described in Das, *9,11-Epoxy-9-homoprosta-5-enoic Acid Analogues as Thromboxane A$_2$ Receptor Antagonists, Journal of Medicinal Chemistry*, volume 33, No. 6, pages 1741–1748 (1990), for the conversion of [1S-[1α, 2α(Z), 3α(1E, 3S, 4R)), 4α]]-7-[3-[4-phenyl-3-(tetrahydropyran-2-yloxy)-1-pentyl]-7-oxabicyclo[2.2.1]hept-2-yl]-5-heptenoic acid to [1S-[1α, 2α(Z), 3α(1E, 3S, 4R)), 4α]]-[[4-[3-(3-hydroxy-4-phenyl-1-pentyl)-7-oxabicyclo[2.2.1]hept-2-yl]-5-heptenoic acid.

The 3-0-DPs, wherein G is formula (iii), may be prepared from (5Z, 13E)-9S, 11R, 15S)- 15 cyclohexyl-9-hydroxy-3-oxa-11,15-bis (tetrahydropyran-2-yloxy)-16, 17, 18, 19, 20-pentanor-5,13-prostanoic acid tert butyl ester (EP 299 914) by the method described in Bundy, *Synthesis and Platelet Aggregation Inhibiting Activity of Prostaglandin D Analogues, Journal of Medicinal Chemistry*, volume 26, pages 790–799 (1983), the entire contents of which are incorporated herein by reference.

The 3-O-DPs of the present invention may be formulated in various pharmaceutical compositions for administering to humans and other mammals as a treatment of glaucoma or ocular hypertension.

The compounds of formula (II) are useful in lowering intraocular pressure and thus are useful in the treatment of glaucoma. As used herein, the term "pharmaceutically effective amount" refers to that amount of a compound of the present invention which lowers IOP when administered to a mammal. The preferred route of administration is topical. The compounds of the present invention can be administered as solutions, suspensions, or emulsions (dispersions) in a suitable ophthalmic vehicle.

In forming compositions for topical administration, the compounds of the present invention are generally formulated as between about 0.00003 to about 0.5 percent by weight (wt %) solutions in water at a pH between 4.5 to 7.4. The compounds are preferably formulated as between about 0.0005 to about 0.03 wt% and, most preferably, between about 0.001 and about 0.01 wt %. While the precise regimen is left to the discretion of the clinician, it is recommended that the resulting solution be topically applied by placing one drop in each eye one or two times a day.

Other ingredients which may be desirable to use in the ophthalmic preparations of the present invention include preservatives, co-solvents and viscosity building agents.

Preferred formulations of 3-O-DPs of the present invention include the following Examples 1–3:

Example 1

| Ingredient | Amount (wt %) |
| --- | --- |
| 3-O-DP | 0.001 |
| Phosphate Buffered Saline | 1.0 |
| Polysorbate 80 | 0.5 |
| Purified water | q.s. to 100% |

Example 2

| Ingredient | Amount (wt %) |
| --- | --- |
| 3-O-DP | 0.001 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| Cremophor EL | 0.1 |
| Benzalkonium chloride | 0.01 |
| HCl and/or NaOH | pH 7.3–7.4 |
| Purified water | q.s. to 100% |

Example 3

| Ingredient | Amount (wt %) |
| --- | --- |
| 3-O-DP | 0.0005 |
| Phosphate Buffered Saline | 1.0 |
| Hydroxypropyl-β-cyclodextrin | 4.0 |
| Purified water | q.s. to 100% |

What is claimed is:

1. A method of treating glaucoma or ocular hypertension in mammals which comprises administering to the mammal a pharmaceutically effective amount of a DP-agonist of formula (II):

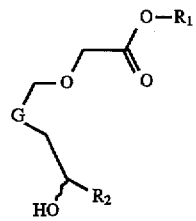

wherein:
$R_1$ is H, alkyl or alkylcycloalkyl;
$R_2$ is alkyl, cycloalkyl or alkylcycloalkyl; and
G is

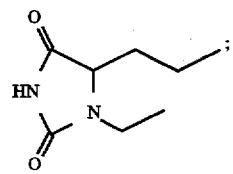

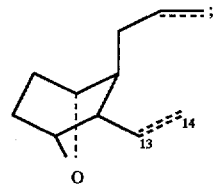

or

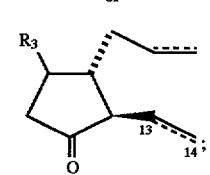

wherein:
$R_3$ is H, OH or alkyl;
--- represents a single bond or double bond; provided that double bonds between the 13 and 14 position are in the trans configuration; and pharmaceutically acceptable salts thereof.

2. The method of claim 1, wherein G is (i).
3. The method of claim 1, wherein G is (ii).
4. The method of claim 1, wherein G is (iii).
5. The method of claim 1, wherein $R_1$ is isopropyl and $R_2$ is cyclohexyl.
6. The method of claim 2, wherein $R_1$ is isopropyl, and $R_2$ is cyclohexyl.
7. The method of claim 3, wherein $R_1$ is isopropyl, and $R_2$ is cyclohexyl.
8. The method of claim 4, wherein $R_1$ is isopmpyl, and $R_2$ is cyclohexyl.

* * * * *